US009861752B2

(12) United States Patent
Buder et al.

(10) Patent No.: US 9,861,752 B2
(45) Date of Patent: Jan. 9, 2018

(54) MIXING NOZZLE

(71) Applicant: Covidien LP, Mansfield, MA (US)

(72) Inventors: Christopher Buder, Sharon, MA (US);
Andrew Koss, Middleboro, MA (US);
Anastasia Righter, Millford, MA (US)

(73) Assignee: Covidien LP, Mansfield, MA (US)

( * ) Notice: Subject to any disclaimer, the term of this patent is extended or adjusted under 35 U.S.C. 154(b) by 102 days.

(21) Appl. No.: 14/687,246

(22) Filed: Apr. 15, 2015

(65) Prior Publication Data

US 2015/0297834 A1 Oct. 22, 2015

Related U.S. Application Data

(60) Provisional application No. 61/981,338, filed on Apr. 18, 2014.

(51) Int. Cl.
*A61M 5/24* (2006.01)
*A61M 5/00* (2006.01)
*A61M 5/28* (2006.01)
*B01F 5/00* (2006.01)
*B01F 13/00* (2006.01)
*A61B 17/00* (2006.01)

(52) U.S. Cl.
CPC .......... *A61M 5/2448* (2013.01); *A61B 17/00* (2013.01); *A61M 5/007* (2013.01); *A61M 5/284* (2013.01); *B01F 5/0077* (2013.01); *B01F 13/0023* (2013.01); *A61B 2017/00495* (2013.01); *B01F 2215/0039* (2013.01)

(58) Field of Classification Search
CPC .... A61M 5/2448; A61M 5/007; A61M 5/284; B01F 13/0023; B01F 5/0077; B01F 2215/0039
See application file for complete search history.

(56) References Cited

U.S. PATENT DOCUMENTS

| 2,708,438 A | 5/1955 | Cohen |
| 3,927,868 A * | 12/1975 | Moore ...................... B01F 3/10 |
| | | 206/221 |
| 4,040,420 A | 8/1977 | Speer |
| 4,261,481 A * | 4/1981 | Speer ................... B01F 5/0645 |
| | | 222/135 |

(Continued)

FOREIGN PATENT DOCUMENTS

| EP | 2111918 A2 | 10/2009 |
| EP | 2145599 A1 | 1/2010 |

(Continued)

OTHER PUBLICATIONS

International Search Report and Written Opinion of International Application No. PCT/US2015/025902, dated Jul. 14, 2015, 13 pp.

(Continued)

*Primary Examiner* — Bradley Osinski
(74) *Attorney, Agent, or Firm* — Shumaker & Sieffert, P.A.

(57) ABSTRACT

A mixing nozzle includes at least two individual mixing channels dimensioned to create a turbulent flow effect to facilitate dispersion of the components of a medical agent, such as a liquid embolic composition, during delivery, e.g., to vasculature of a subject. In some examples, the mixing nozzle is configured to be mechanically and fluidically connected to a syringe, a catheter, or both the syringe and the catheter.

30 Claims, 7 Drawing Sheets

(56) References Cited

U.S. PATENT DOCUMENTS

| | | | |
|---|---|---|---|
| 4,583,978 | A | 4/1986 | Porat |
| 5,116,315 | A | 5/1992 | Capozzi et al. |
| 5,512,054 | A | 4/1996 | Morningstar |
| 5,531,710 | A | 7/1996 | Dang |
| 5,580,568 | A | 12/1996 | Greff et al. |
| 5,630,800 | A | 5/1997 | Blank |
| 5,667,767 | A | 9/1997 | Greff et al. |
| 5,694,480 | A | 12/1997 | Itakura |
| 5,851,508 | A | 12/1998 | Greff et al. |
| 6,033,427 | A | 3/2000 | Lee |
| 6,386,872 | B1 | 5/2002 | Mukasa |
| 6,511,472 | B1 | 1/2003 | Hayman |
| 7,018,089 | B2 | 3/2006 | Wenz |
| 9,326,829 | B2 | 5/2016 | Kojima |
| 2006/0071025 | A1 | 4/2006 | Crews |
| 2009/0118703 | A1 | 5/2009 | Orilla |
| 2009/0247985 | A1* | 10/2009 | Melsheimer ..... A61B 17/12022 604/506 |
| 2010/0049165 | A1 | 2/2010 | Sutherland |
| 2010/0100099 | A1 | 4/2010 | Reilly |
| 2010/0305514 | A1 | 12/2010 | Valenti |
| 2011/0027751 | A1 | 2/2011 | Kojima |
| 2011/0121035 | A1 | 5/2011 | Greter et al. |
| 2011/0139821 | A1 | 6/2011 | Greter et al. |
| 2013/0126559 | A1 | 5/2013 | Cowan |
| 2013/0269806 | A1 | 10/2013 | Burns |
| 2013/0338643 | A1 | 12/2013 | De Silva |
| 2014/0048556 | A1* | 2/2014 | Pearcy ................. A61M 5/284 222/1 |
| 2014/0257233 | A1 | 9/2014 | Cowan |
| 2016/0296703 | A1 | 10/2016 | Bailey |

FOREIGN PATENT DOCUMENTS

| | | |
|---|---|---|
| JP | 2002282368 | 10/2002 |
| WO | 0187389 A1 | 11/2001 |
| WO | 0205898 A1 | 1/2002 |
| WO | 03039375 A2 | 5/2003 |
| WO | 2004047651 A2 | 6/2004 |
| WO | 2005048977 A2 | 6/2005 |
| WO | 2007089948 A2 | 8/2007 |

OTHER PUBLICATIONS

U.S. Appl. No. 14/687,079, by Christopher Buder, filed Apr. 15, 2015.

Office Action from U.S. Appl. No. 14/687,079, dated Mar. 14, 2017, 18 pp.

"Connected", Merriam-Webster definition, retrieved from https://www.merriam-webster.com/dictionary/connected, accessed on Nov. 2016, 1 pp.

"Head", Merriam-Webster definition, retrieved from https://www.merriam-webster.com/dictionary/head, accessed on Nov. 2016, 2 pp.

Communication Pursuant to Rules 161(1) and 162 EPC dated Nov. 25, 2016 from counterpart European Application No. 15719096.8, 2 pp.

Examination Report from counterpart European Application No. 15719096.8, dated Nov. 13, 2017, 5 pp.

* cited by examiner

MIXING NOZZLE

This application claims the benefit of U.S. Provisional Patent Application No. 61/981,338, which was filed on Apr. 18, 2014 and is entitled, "MIXING SYRINGE AND NOZZLE," the entire content of which is incorporated herein by reference.

TECHNICAL FIELD

The present disclosure generally relates to the mixing of a fluid for delivery of a medical agent to a subject, and, in particular, relates to a method and device for mixing and delivering liquid embolic compositions to the vasculature of a subject.

BACKGROUND

The delivery of fluid compositions which solidify in vivo is useful for numerous vascular applications including the occlusion of neurovascular aneurysms, arteriovenous malformations ("AVMs"), arteriovenous fistulas ("AVF"), abdominal aortic aneurysm Type 1 and Type 2 endoleaks, bleeding, tumors (including hypervascular tumors), varicose seals, and portal vein embolization, as well as in the sterilization of mammals and the treatment of urinary incontinence. Some liquid embolic compositions include a water insoluble, biocompatible, non-biodegradable polymer, dissolved in a biocompatible solvent. These liquid embolic compositions can include a water insoluble, radiopaque material or contrast agent to permit the clinician to visualize delivery of the composition to the vascular treatment site via conventional techniques such as fluoroscopy.

Liquid embolic compositions may be delivered via a catheter technique that permits the clinician to selectively place the catheter at any desired location within the vasculature. A catheter tip is directed to the desired location by use of a visualization technique, such as fluoroscopy. The liquid embolic composition is delivered to the catheter through a syringe connected to the catheter hub. Some current practices require the liquid embolic composition to be continuously mixed for 20 minutes in a vial to achieve adequate suspension of the contrast agent during delivery. Inadequate mixing or delays in delivery after mixing may result in contrast agent settling, causing poor visualization of the liquid embolic composition during injection. Accurate visualization helps ensure that the liquid embolic composition is being delivered to the intended vascular site, to detect undesired reflux of the liquid embolic composition on the catheter tip, or to detect premature solidification of the liquid embolic composition causing catheter or branch vessel occlusion.

SUMMARY

The present disclosure describes a medical method that includes fluidly coupling a mixing nozzle to a fluid housing of a syringe, the fluid housing containing a liquid embolic composition therein, the liquid embolic composition including a contrast agent, directing the liquid embolic composition to the mixing nozzle, and distributing the liquid embolic composition through at least two individual mixing channels of the mixing nozzle to facilitate dispersion of the contrast agent within the liquid embolic composition.

In some embodiments, distributing the liquid embolic composition includes passing the liquid embolic composition through at least four individual mixing channels of the mixing nozzle.

In some embodiments, the mixing nozzle may include a nozzle inlet defining an inlet chamber in fluid communication with the at least two individual mixing channels, and wherein directing the liquid embolic composition includes delivering the liquid embolic to the inlet chamber for passage through the at least two individual mixing channels.

In some embodiments, the mixing nozzle includes a nozzle outlet defining an outlet chamber in fluid communication with the at least two individual mixing channels, and wherein distributing the liquid embolic composition includes delivering the liquid embolic composition to the outlet chamber subsequent to passage through the at least two individual mixing channels.

In some embodiments, the at least two individual mixing channels each define radial and longitudinal components of direction relative to a longitudinal axis of the mixing nozzle, and wherein distributing the liquid embolic composition includes passing the liquid embolic composition along a radial and longitudinal path defined by each of the at least two mixing channels.

In some embodiments, directing the liquid embolic composition includes advancing a plunger through the fluid housing of the syringe to deliver the liquid embolic composition through a housing outlet of the fluid housing and to the mixing nozzle.

In some embodiments, the method further comprises accessing vasculature of a subject with a catheter, fluidly coupling the mixing nozzle to the catheter, and directing the liquid embolic composition relative to an intravascular site within the vasculature.

In some embodiments, the at least two individual mixing channels intersect with each other prior to reaching a nozzle outlet of the mixing nozzle.

The present disclosure also describes a medical apparatus that comprises a mixing nozzle including a nozzle inlet configured to couple to a syringe containing a medical agent, a nozzle outlet, and a nozzle body disposed between the nozzle inlet and the nozzle outlet, the nozzle body defining a longitudinal axis and including at least two individual mixing channels in fluid communication with the nozzle inlet and with the nozzle outlet, at least one mixing channel of the at least two mixing channels defining a flow path having longitudinal and radial components of direction with respect to the longitudinal axis defined by the nozzle body. The apparatus may be used to mix the medical agent stored within the syringe.

In some embodiments, each of the at least two mixing channels defines a flow path having longitudinal and radial components of direction with respect to the longitudinal axis defined by the nozzle body. In some embodiments, the nozzle body defines at least four individual mixing channels.

In some embodiments, each of the at least two mixing channels defines an arcuate flow path.

In some embodiments, the nozzle inlet defines an inlet chamber for receiving the medical agent with the inlet chamber being in fluid communication with each of the at least two mixing channels. In some embodiments, the nozzle outlet defines an outlet chamber in fluid communication with the at least two individual mixing channels. The medical agent can be delivered from the at least two individual mixing channels to the outlet chamber.

In some embodiments, the nozzle inlet includes a screw thread configured to releasably couple the nozzle to the syringe.

In some embodiments, a syringe is provided. The syringe configured to releasably couple to the mixing nozzle. The syringe includes a liquid embolic composition including a contrast agent. In some embodiments, a catheter may be coupled to the mixing nozzle.

In some embodiments, the nozzle inlet includes a frangible compartment. The frangible compartment may include a contrast agent.

In some embodiments, the at least two individual mixing channels intersect with each other prior to reaching a nozzle outlet of the mixing nozzle.

The present disclosure also describes a medical system includes a syringe, a liquid composition stored within the syringe, and a mixing nozzle configured to releasably couple to the syringe. The mixing nozzle includes a nozzle inlet, a nozzle outlet and a nozzle body disposed between the nozzle inlet and the nozzle outlet. The nozzle body defines at least two individual mixing channels in fluid communication with the nozzle inlet and with the nozzle outlet.

In some embodiments, each of the at least two mixing channels defines a flow path having longitudinal and radial components of direction with respect to a longitudinal axis defined by the nozzle body. Each of the at least two mixing channels may define an arcuate flow path. In some embodiments, each arcuate flow path is dimensioned to diverge outwardly relative to the longitudinal axis from the nozzle inlet toward a median transverse axis bisecting the nozzle body, and is dimensioned to converge inwardly from the median transverse axis toward the nozzle outlet.

In some embodiments, the nozzle outlet defines an outlet chamber in fluid communication with the at least two individual mixing channels whereby the mixing nozzle is configured to deliver the liquid composition from the at least two individual mixing channels to the outlet chamber for further mixing within the outlet chamber.

In some embodiments, the syringe comprises a plunger at least partially disposed within a fluid housing defining a housing outlet of the syringe. The plunger is configured to be advanced within the fluid housing to deliver the liquid composition through a housing outlet of the fluid housing.

In some embodiments, the liquid composition includes a liquid embolic and a contrast agent.

In some embodiments, the at least two individual mixing channels intersect with each other prior to reaching a nozzle outlet of the mixing nozzle.

The present disclosure is also directed a method of making a mixing nozzle. In addition, the method may further comprise introducing a medical agent into the fluid housing of the syringe.

The present disclosure is also directed a method assembling a system that includes a syringe, a mixing nozzle, and in some examples, a catheter. The method can include coupling the syringe to a nozzle inlet of the mixing nozzle, and coupling the catheter to a nozzle outlet of the mixing nozzle.

Embodiments can include one or more of the following advantages.

The mixing nozzle described herein is configured to relatively uniformly mix a medical agent, such as a liquid embolic composition containing a contrast agent, and deliver the mixed medical agent to a catheter or conduit accessing, e.g., the vasculature of a subject. The mixing nozzle includes mixing channels advantageously configured to create a turbulent effect within the medical agent thereby mixing and distributing the contents of the agent, and, in the case of a liquid embolic composition, suspending the contrast agent throughout the composition. The mixing nozzle may eliminate the need to mix the components of the liquid embolic composition prior to the procedure, thereby avoiding spills, reducing treatment time and maximizing clinician efficiency. In addition, the relatively uniform mixing of the liquid embolic agent by the mixing nozzle may improve the visualization of the liquid embolic composition during injection into a subject.

Other advantages will become apparent by the following description.

DETAILED DESCRIPTION

Figure 1:
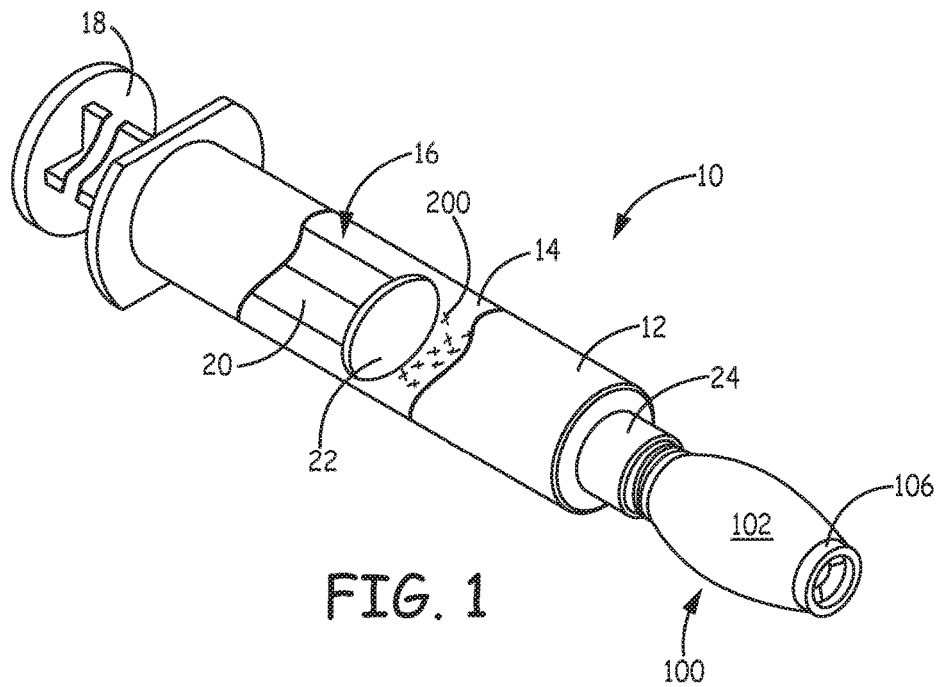
FIG. 1 is a perspective view of an example mixing nozzle illustrated coupled to an example syringe with portions of the syringe removed.

Particular embodiments of the present disclosure are described below with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure. Like reference numerals may refer to similar or identical elements throughout the description of the figures.

Figure 2:
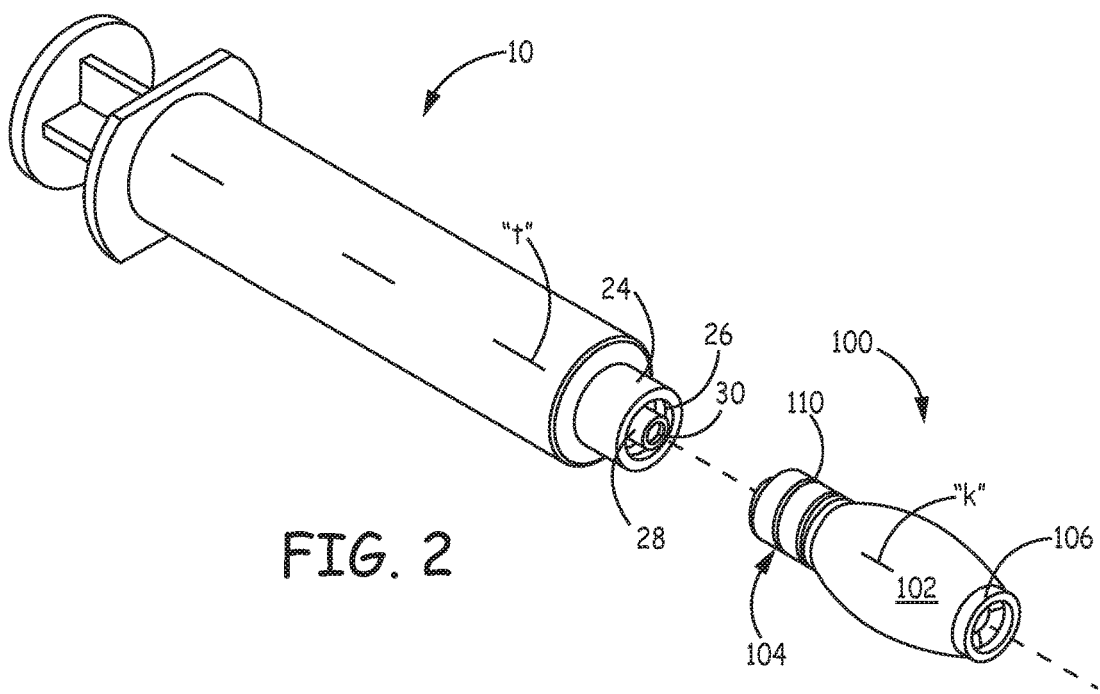
FIG. 2 is a perspective view of the mixing nozzle of FIG. 1, uncoupled from the syringe.
Figure 3:
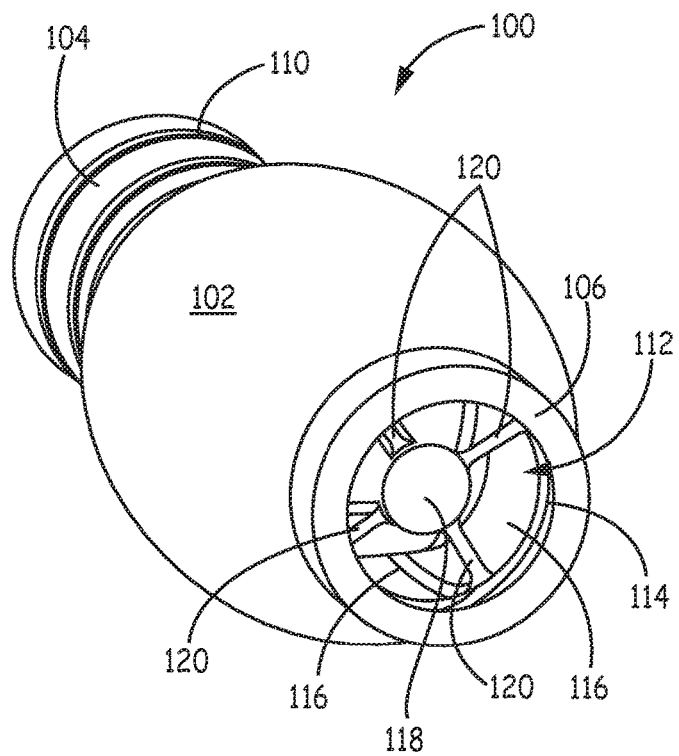
FIG. 3 is a perspective view of the mixing nozzle of FIG. 1.
Figure 4:
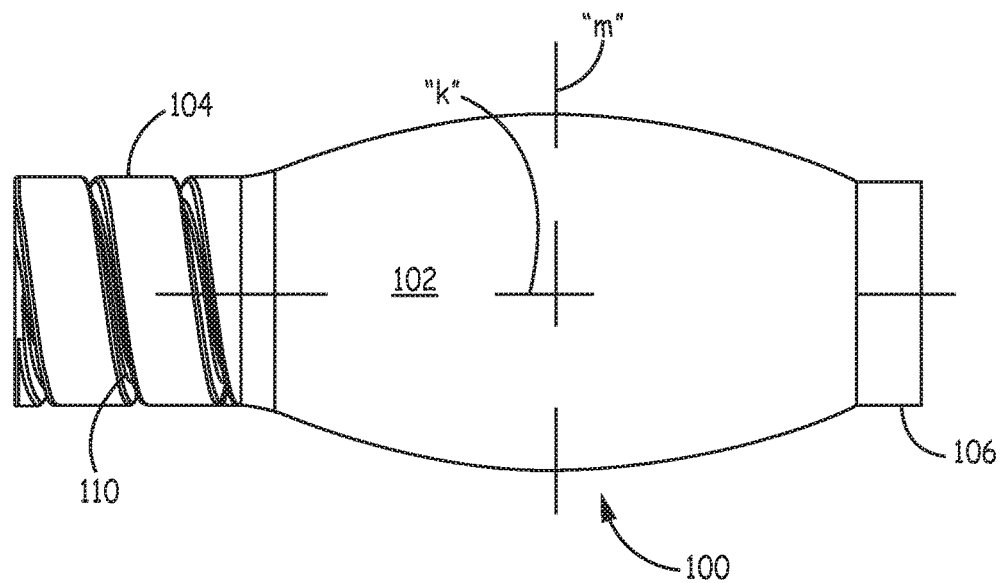
FIG. 4 is a side elevation view of the mixing nozzle of FIG. 1.
Figure 5:
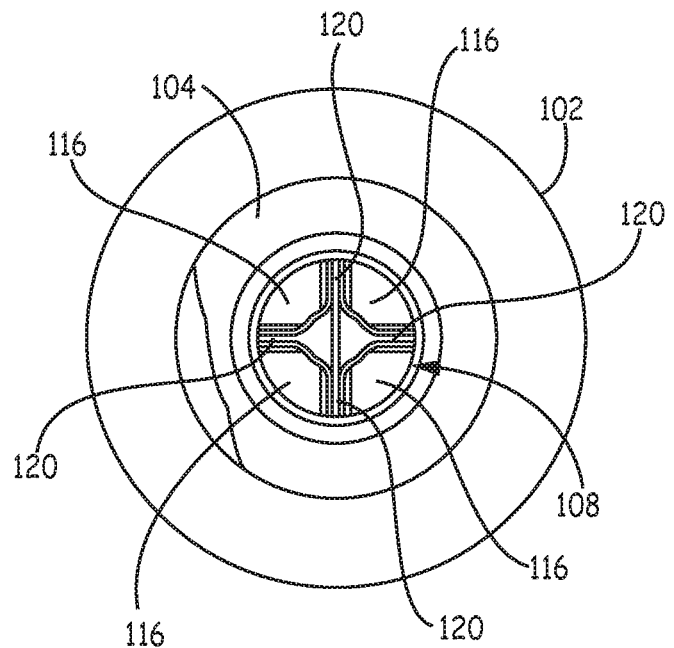
FIG. 5 is an axial view of the nozzle inlet of the mixing nozzle of FIG. 1.
Figure 6:
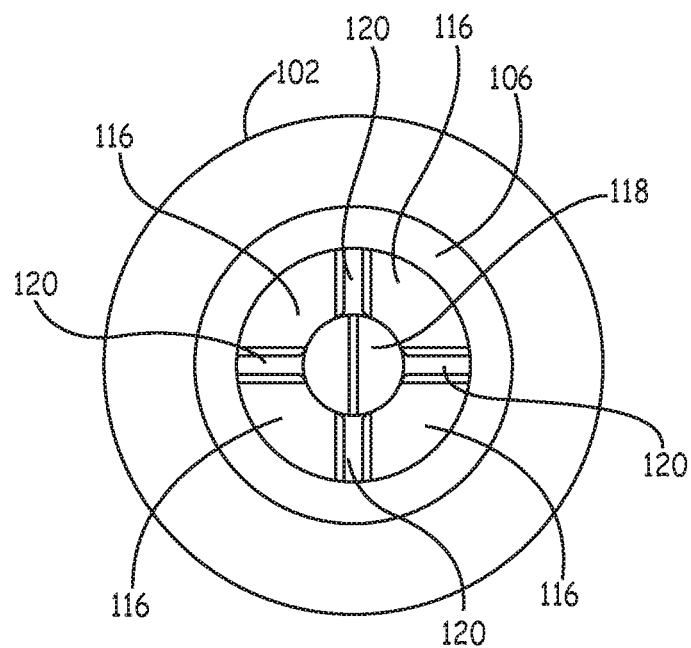
FIG. 6 is an axial view of the nozzle outlet of the mixing nozzle of FIG. 1.
Figure 7:
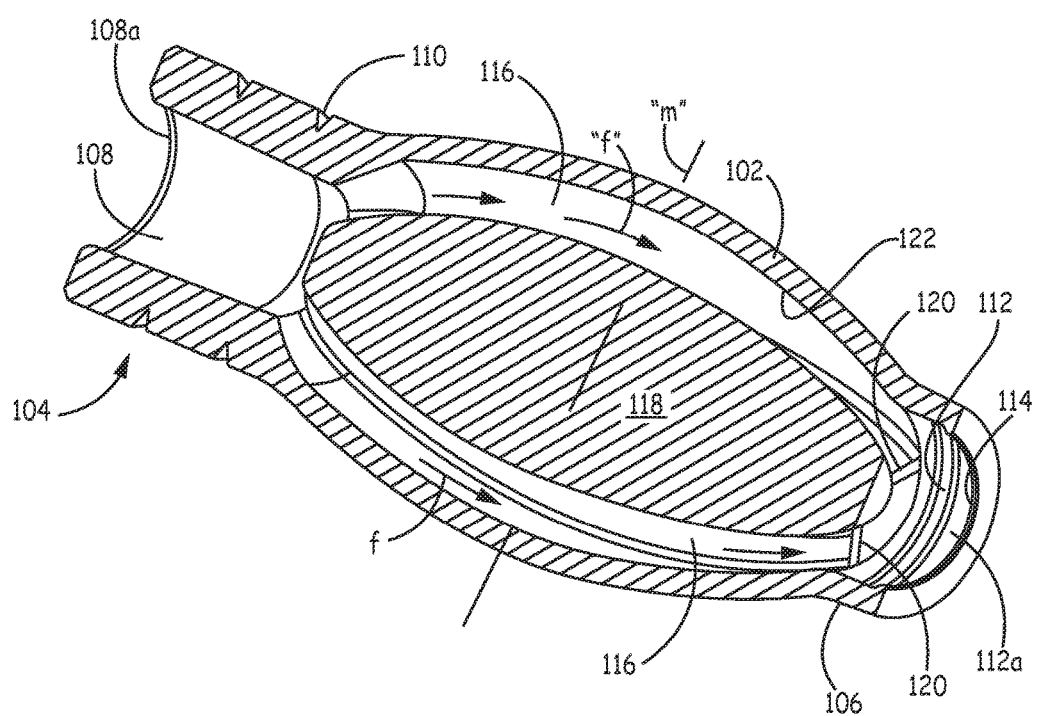
FIG. 7 is a perspective view in cross-section of the mixing nozzle of FIG. 1.

FIGS. 1 and 2 illustrate an example syringe 10 and an example mixing nozzle 100 in accordance with the present disclosure. The syringe 10 may be any device suitable for storing and delivering a medical agent to a subject. In the embodiment of FIGS. 1 and 2, the syringe 10 is in the form of a manually operated syringe having a medical agent contained or stored therein. In some examples, the medical agent may include a liquid embolic composition and a contrast agent useful in vascular treatments. The syringe 10 is fluidly coupled to the mixing nozzle 100. The mixing nozzle 100 has a nozzle inlet 104, a nozzle outlet 106, and at least two mixing channels 116 (e.g., shown in FIGS. 3 and 5-8) defining multiple flow paths "f" (e.g., shown in FIG. 7) for the medical agent. The medical agent flows from the syringe 10, into the at least two mixing channels 116, and then converges back to a single chamber for distribution through a catheter accessing vasculature of a subject.

The mixing channels 116 advantageously increase the surface area within the mixing nozzle 100 to which the medical agent is exposed, thereby facilitating mixing of the components of the medical agent as the medical agent flows through the channels 116. The separation of the medical agent into the isolated chambers of the mixing channels 116 and subsequent remixing adjacent the nozzle outlet 106 further facilitates mixing and suspension/resuspension of, e.g., the contrast agent of the liquid embolic composition in examples in which the medical agent is or otherwise includes a liquid embolic composition, throughout the liquid embolic composition.

Referring now to FIGS. 3-7, in conjunction with FIGS. 1 and 2, the mixing nozzle 100 will be described. The mixing nozzle 100 includes a nozzle body 102 defining a longitudinal axis "k" and a median transverse axis "m" bisecting the nozzle body 102. The mixing nozzle 100 further defines a nozzle inlet 104 and a nozzle outlet 106 adjacent respective longitudinal ends of the nozzle body 102. The nozzle inlet 104 is adapted for connection to the syringe 10 and defines an inlet chamber 108 leading to an inlet opening 108a (FIGS. 5 and 7), which can be positioned at the end of the nozzle body 102 The inlet chamber 108 is configured to receive the medical agent distributed by the syringe 10. The nozzle inlet 104 includes a connecting structure, e.g., in the form of an external thread(s) 110, configured to mechanically couple the nozzle body 102 to a corresponding structure of the syringe 10 in a manner that releasably couples the components. In some examples, the releasable coupling may permit the nozzle 100 and the syringe 10 to be separate components and subsequently attached to each other, e.g., by a clinician. In addition, in some examples, the releasable coupling may permit the nozzle 100 and the syringe 10 to be detached from each other without substantially damaging the structure of the nozzle 100 and the syringe. Other forms of connecting structures can be used in other examples, such as, but not limited to, a bayonet coupling, an interference fit, or the like.

The nozzle outlet 106 defines an outlet chamber 112 in which the medical agent passing through the nozzle body 102 is received. The outlet chamber 112 leads to an outlet opening 112a, which may be positioned at an end of the nozzle body 102. The outlet chamber 112 may include a connecting structure configured to mechanically couple the nozzle body 102 to a microcatheter. In some embodiments, the connecting structure includes internal thread(s) 114 within the wall of the nozzle outlet 106. In other examples, other forms of connecting structures can be used, such as the ones described above with respect to the nozzle inlet 104.

The nozzle body 102 has at least two individual mixing channels 116 in fluid communication with the nozzle inlet 104 and the nozzle outlet 106. At least one or more of the mixing channels 116 may define a flow path "f" (FIG. 7) having longitudinal and radial components of direction with respect to the longitudinal axis "k" defined by the nozzle body 102. In one embodiment, four mixing channels 116 are provided with each of the mixing channels 116 having longitudinal and radial components of direction. In other embodiments, the nozzle body 102 can define more than four or less than four mixing channels 116. In some examples, the mixing channels 116 may be radially spaced from each other at predefined intervals, e.g., ninety (90) degree intervals with respect to the longitudinal axis "k" in examples in which there are four mixing channels 116. Non-uniform arrangements of the mixing channels 116 can also be used in other examples. The mixing channels 116 may be independent of each other within the nozzle body 102 (e.g., defining fluidically separate flow paths through the nozzle body 102) and, in some examples, may intersect to provide varying flow paths through the nozzle body 102.

The mixing channels 116 further may define an arcuate characteristic or profile to provide arcuate flow paths "f" through the nozzle body 102. Each arcuate flow path "f" diverges outwardly relative to the longitudinal axis "k" from the nozzle inlet 104 toward the median transverse axis "m", and then converges inwardly from the median transverse axis "m" toward the nozzle outlet 106.

In some embodiments, the mixing channels 116 are each defined between an inner central hub 118 and adjacent spokes 120 which depend from the central hub 118 and connect to the inner wall 122 of the nozzle body 102. The central hub 118 defines a cross-section or diameter which gradually increases from the nozzle inlet 104 toward the median transverse axis "m" and decreases from the median axis "m" toward the nozzle outlet 106. This configuration increases the surface area to which the medical agent is exposed as the agent flows through the mixing nozzle 100. This increased surface area, division of the medical agent into isolated chambers of the mixing channels 116, and the configuration of the multi-directional flow paths may facilitate mixing of the components of the medical agent for distribution to the subject, as discussed in further detail below.

Referring again to FIGS. 1 and 2, the syringe 10 may be any conventional distribution device adapted for containing and distributing a medical agent, e.g., a liquid embolic composition. The syringe 10 may include a fluid housing 12 defining a longitudinal axis "t" and an internal chamber 14 configured to store the medical agent. A plunger 16 is at least partially disposed within the fluid housing 12 and is adapted to move or advance in a general longitudinal direction (parallel to longitudinal axis "t") within the internal chamber 14. The plunger 16 may be manually actuated by a clinician or may be activated with the assistance of a device, such as an electro-mechanical system including a pump or pneumatically driven piston. In FIG. 1, the plunger 16 is shown in an unactuated position. The plunger 16 may include a plunger grip 18, a plunger shaft 20 depending from the plunger grip 18 and a plunger head 22 attached to the remote end of the plunger shaft 20 (opposite the grip 18). In some examples, the plunger head 22 may be dimensioned to establish a sealing relation with the inner wall surface of the fluid housing 12, and may be formed of an elastomeric or resilient material, such as rubber.

The fluid housing 12 further defines a housing connector 24 which is configured to releasably couple with the mixing nozzle 100. In some embodiments, the housing connector 24 includes connecting structure, e.g., in the form of an internal thread 26, which is configured to cooperate with a corresponding structure of the nozzle inlet 104 (e.g., the external thread 110 of the nozzle inlet 104) of the mixing nozzle 100 to effect the releasable coupling of the components. A housing outlet 28 is concentrically arranged within the housing connector 24, and defines an outlet opening 30 configured to be in fluid communication with the internal chamber 14 of the fluid housing 12 when the nozzle 100 is coupled to the syringe 10. In this manner, the outlet opening 30 may direct fluid from the internal chamber 14 to the nozzle 100 upon actuation of the plunger 16. In some examples, an end cap (not shown) may be mountable to the housing outlet 28 to enclose the medical agent within the internal chamber 14 of the fluid housing 12, e.g., prior to connecting the nozzle 100 to the syringe 10. The end cap may be removed from the housing outlet 28 prior to connecting the nozzle 100 to the syringe 10.

In some examples, the syringe 10 may be prefilled with the medical agent, e.g., a liquid embolic composition 200 (FIG. 1), and sealed until the medical procedure is to be performed. The liquid embolic composition 200 may include any liquid biocompatible polymer(s), solvent(s) etc. for facilitating embolization of a vascular malformation, and a contrast agent. The contrast agent may be water insoluble and include tantalum, tantalum oxide, barium sulfate, gold, tungsten, or platinum. These water insoluble contrast agents may be in particle or powder form, and may have an average particle size of about 10 μm or less.

One suitable embolic is the embolic composition ONYX® sold by Covidien LP, Irvine, Calif. ONYX® includes an EVOH (ethylene vinyl alcohol) copolymer dissolved in DMSO (dimethyl sulfoxide), and suspended micronized tantalum powder to provide contrast for visualization under fluoroscopy. Although some figures are described with respect to liquid embolic composition 200, in other examples, the mixing nozzle 100 described herein can be used to deliver other medical agents.

Figure 8:
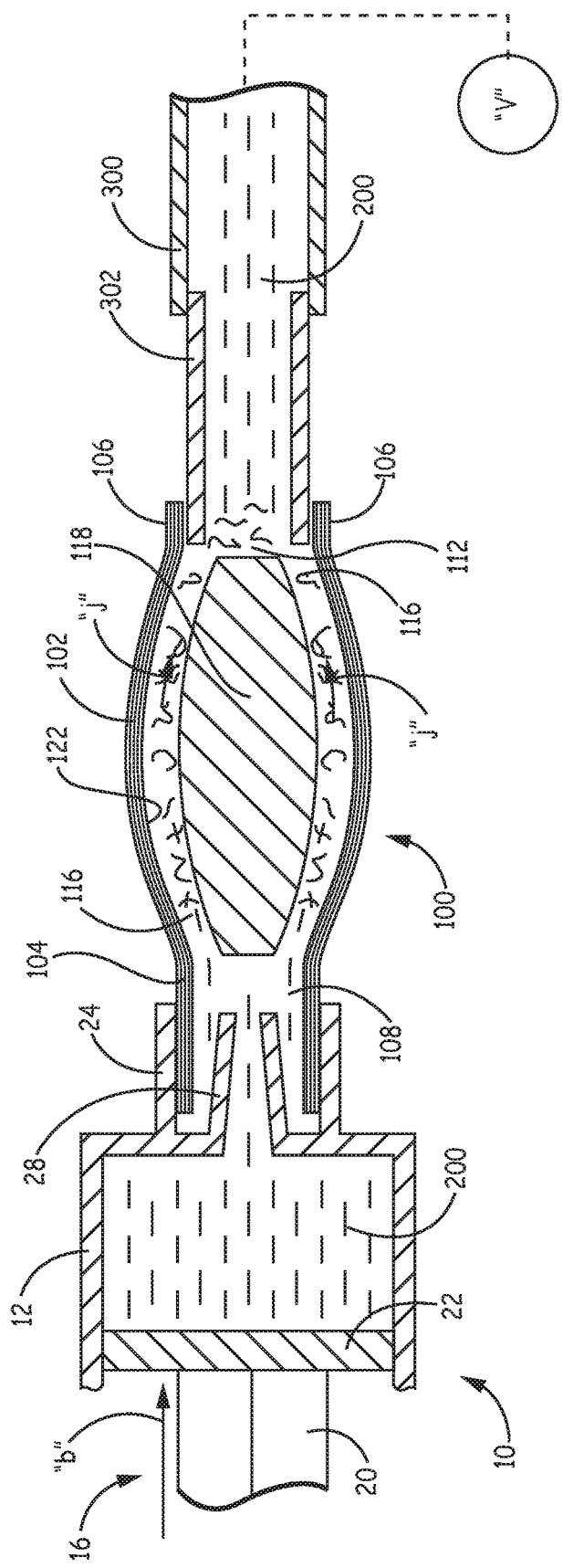
FIG. 8 is a side cross-sectional view of the syringe and the mixing nozzle of FIG. 1 coupled to an example catheter for delivering a liquid embolic composition to vasculature of a subject.

The use of the mixing nozzle 100 and the syringe 10 for relatively uniformly mixing and delivering the liquid embolic composition 200 to a subject will now be discussed. Referring now to FIG. 8, the mixing nozzle 100 is connected to the syringe 10 through threaded coupling of the external thread 110 of the nozzle inlet 104 with the cooperating internal thread 26 of the housing connector 24 of the syringe 10. The nozzle outlet 106 of the mixing nozzle 100 may be connected to a catheter, e.g., a microcatheter 300. The catheter may, for example, be accessing a malformation, identified schematically as "v" within the peripheral vasculature or neurovasculature. In some embodiments, a luer connector 302 of the microcatheter 300 is coupled to the nozzle outlet 106 through e.g., threaded cooperation of the internal thread 114 within the nozzle outlet 106 and a corresponding thread (not shown) of the luer connector 302.

The procedure is continued by advancing the plunger 16 in the direction of directional arrow "b" to force the liquid embolic composition 200 to be discharged through the housing outlet 28 of the syringe 10 and enter the inlet chamber 108 of the nozzle inlet 104 of the mixing nozzle 100. Continued advancing movement of the plunger 16 forces the liquid embolic composition 200 under pressure to be subdivided and passed through the mixing channels 116 of the nozzle body 102. As the liquid embolic composition 200 passes through the mixing channels 116, the increased resistive surface contact with the central hub 118, spokes 120 and the interior wall 122 of the nozzle body 102, and the isolated and/or multi-directional flow paths "f" of the mixing channels 116, create a turbulent flow effect, identified schematically as indicator "j", consisting of, e.g., mini-swirls, eddies and/or wakes, within the liquid embolic composition 200. This turbulent effect "j" mixes and helps to relatively uniformly disperse the components, including the contrast agent, in the composition 200 within the channels 116.

The liquid embolic composition 200 is further mixed as the multiple flow paths "f" of the mixing channels 116 converge within the outlet chamber 112 of the nozzle outlet 106. The mixed liquid embolic composition 200 with suspended contrast agent is passed through the microcatheter 300, and delivered to the targeted vascular malformation "v". Confirmation of successful delivery of the liquid embolic composition 200 to the malformation may be ascertained through medical imaging (e.g., fluoroscopy) of the suspended contrast agent with an imaging device.

The mixing nozzle 100 is configured to effectively distribute the components of the liquid embolic composition 200, including the water insoluble contrast agent, relatively uniformly throughout the composition. The turbulent flow effect created by the mixing nozzle 100 may be achieved during activation of the plunger 16 even at relatively low advancing speeds of the plunger 16, i.e., in some examples, the turbulent flow effect may not be dependent on rapid advancement of the plunger 16 and corresponding movement of the liquid embolic composition 200, but may be achieved through normal manual actuation of the plunger 16.

Figure 9:
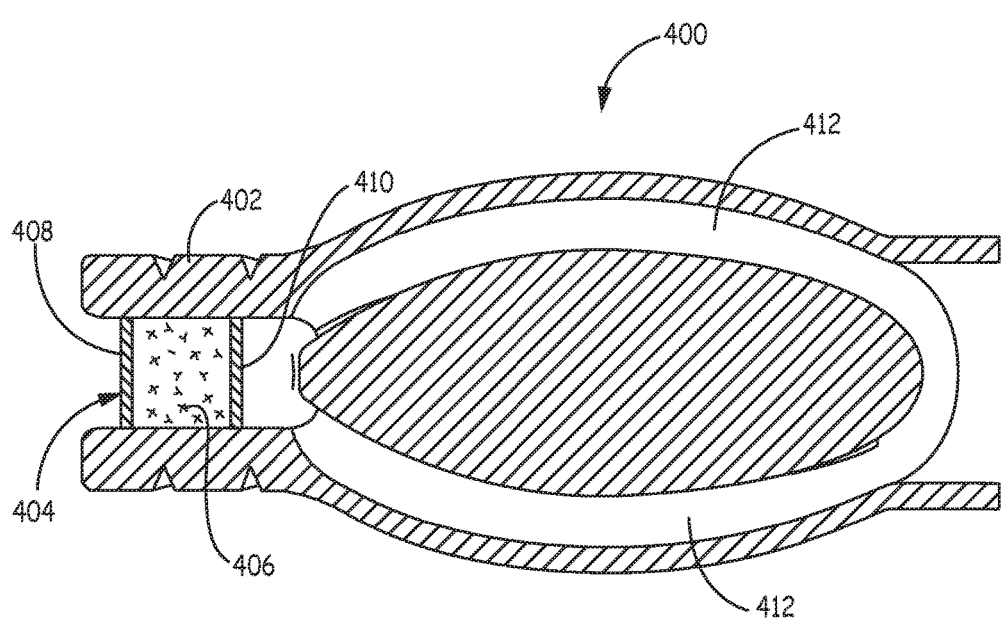
FIG. 9 is a cross-sectional view of an example mixing nozzle that includes a compartment for storing contrast agent.

FIG. 9 is a cross-sectional view of another embodiment of a mixing nozzle 400. The mixing nozzle 400 is substantially similar to the mixing nozzle 100 of FIGS. 1-8. However, the nozzle inlet of 402 of the mixing nozzle 400 includes a compartment 404 for storing contrast agent 406, such as any of the water insoluble contrast agents identified hereinabove. The compartment 404 may be defined and enclosed between two frangible walls 408, 410. The frangible walls 408, 410 may include any material adapted to split, tear or break apart upon engagement with, e.g., the housing outlet 28 of the syringe 10. In one embodiment, the frangible walls 408, 410 each may include a foil liner.

When the housing outlet 28 of the syringe 10 is positioned within the nozzle inlet 402, the frangible walls 408, 410 are torn, releasing the contrast agent 406. Upon passage of the liquid embolic composition 200 from the syringe 10 and through the mixing nozzle 400, the contrast agent 406 is mixed and relatively uniformly distributed via the mixing channels 412 with the remainder of the composition. By the provision of the compartment 404, the contrast agent 406 may be isolated from the liquid embolic, thereby facilitating storage and shelf life of the contrast agent 406, and also eliminating the need to manually mix the contrast agent 406 with the liquid embolics prior to performance of the medical procedure. In an alternate approach, at least the frangible wall 408 may be penetrated with the housing outlet 28 of the syringe 10 or with a needle attachable to the syringe 10, and the contrast agent 406 drawn back into the internal chamber 14 of the fluid housing 12 for initial mixing with the liquid composition 200. Thereafter, the liquid embolic composition is delivered through the mixing nozzle 400 to be mixed in the manner discussed hereinabove, and delivered to the microcatheter.

Figure 10:
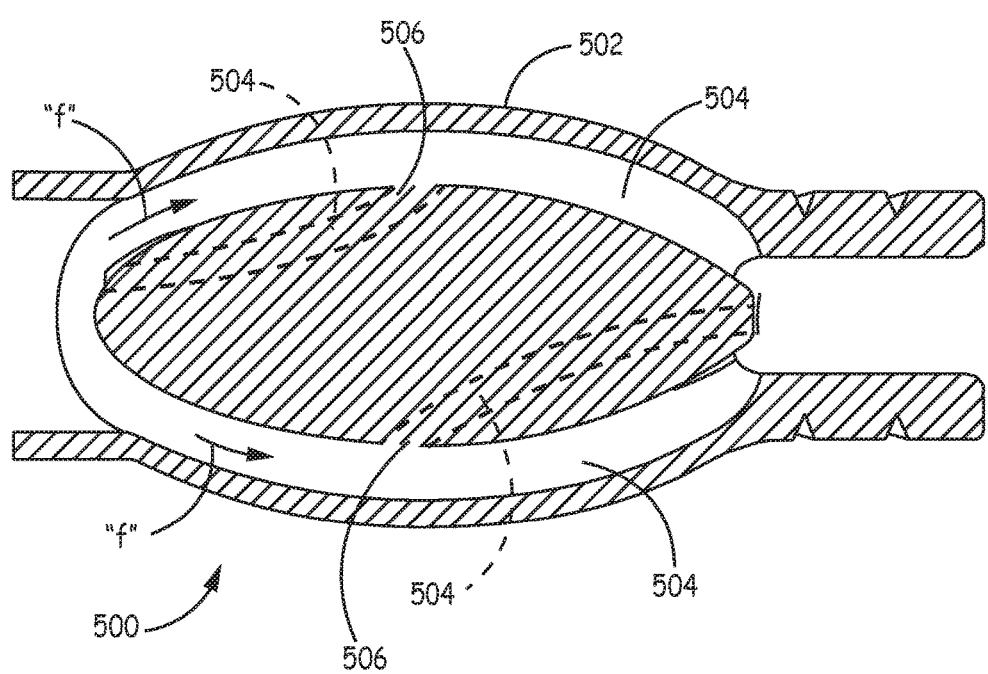
FIG. 10 is a cross-sectional view of an example mixing nozzle that includes intersecting mixing channels.

FIG. 10 is a cross-sectional view of another embodiment of a mixing nozzle 500. The mixing nozzle 500 is substantially similar to the mixing nozzle 100 of FIGS. 1-8. However, the mixing nozzle 500 includes a nozzle body 502 having a plurality of mixing channels 504, e.g., four mixing channels with two channels 504 being shown in phantom, where at least some mixing channels intersect with each other prior to reaching the fluid outlet of the nozzle. For example, in the example shown in FIG. 10, pairs of mixing channels 504 intersect one another at juncture 506, whereby the intersecting fluid paths "f" are in fluid communication. The intersecting channels 504 can provide additional opportunities for the liquid embolic composition to mix and create the turbulent flow effect to place the contrast agent in suspension.

Although the mixing apparatus has been discussed in the context of mixing and delivering an embolic composition having two or more components, including liquid and a water insoluble contrast agent, to vasculature of a subject, the mixing nozzle may be used to mix and deliver an embolic composition having aqueous based contrast agents such as metrizamide, iopamidol, iothalamate sodium, iodomide sodium, and meglumine. In addition or alternatively, the mixing nozzle may be used to mix any medical agent, including single substances or compositions, such as drugs, medicants or the like to the subject for treatment of a number of medical conditions. For example, the mixing nozzle may mix and deliver a medical agent or composition for treatment of blood vessels, tumors, an arteriovenous fistula ("AVF"), uncontrolled bleeding and the like, as well as in the sterilization of mammals by blocking the vas deferens or fallopian tubes, or the treatment of urinary incontinence by the addition of a bulking agent to the periurethral tissue, and the like.

The mixing nozzles described herein may be formed using any suitable technique. For example, the mixing nozzles can be molded as a monolithic structure or as multiple parts that are connected together. The mixing nozzles may be formed of any one or more suitable materials, such as one or more plastic materials.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A method comprising:
   fluidly coupling a mixing nozzle to a fluid housing of a syringe, the fluid housing containing a liquid embolic composition therein, and the liquid embolic composition including a contrast agent, wherein the mixing nozzle comprises:
   a nozzle body;
   a nozzle inlet positioned at a first end of the nozzle body and configured to couple to the syringe; and
   a nozzle outlet positioned at a second end of the nozzle body;
   directing the liquid embolic composition to the mixing nozzle; and
   distributing the liquid embolic composition through at least two individual mixing channels of the mixing nozzle to facilitate dispersion of the contrast agent within the liquid embolic composition, wherein the at least two mixing channels define fluidically separate flow paths that are fluidically separate from each other between the nozzle inlet and the nozzle outlet, wherein the nozzle body defines the at least two individual mixing channels.

2. The method of claim 1, wherein distributing the liquid embolic composition includes passing the liquid embolic composition through at least four individual mixing channels of the mixing nozzle.

3. The method of claim 1, wherein the nozzle inlet defines an inlet chamber in fluid communication with the at least two individual mixing channels and the nozzle outlet defines an outlet chamber in fluid communication with the at least two individual mixing channels,
   wherein directing the liquid embolic composition includes delivering the liquid embolic to the inlet chamber for passage through the at least two individual mixing channels, and
   wherein distributing the liquid embolic composition includes delivering the liquid embolic composition to the outlet chamber subsequent to passage through the at least two individual mixing channels.

4. The method of claim 1, wherein the at least two individual mixing channels each define radial and longitudinal components of direction relative to a longitudinal axis of the mixing nozzle, and wherein distributing the liquid embolic composition includes passing the liquid embolic composition along a radial and longitudinal path defined by each of the at least two mixing channels.

5. The method of claim 1, wherein directing the liquid embolic composition includes advancing a plunger through the fluid housing to deliver the liquid embolic composition through a housing outlet of the fluid housing and to the mixing nozzle.

6. The method of claim 1, further comprising:
   accessing vasculature of a subject with a catheter;
   fluidly coupling the mixing nozzle to the catheter; and
   directing the liquid embolic composition to an intravascular site within the vasculature.

7. The method of claim 1, wherein the mixing nozzle further defines additional mixing channels that intersect with the at least two individual mixing channels prior to the at least two individual mixing channels reaching the nozzle outlet of the mixing nozzle.

8. The method of claim 1, wherein an entirety of the nozzle body is between the nozzle inlet and the nozzle outlet.

9. A medical apparatus comprising:
   a mixing nozzle including:
   a nozzle inlet configured to couple to a syringe containing a medical agent;
   a nozzle outlet; and
   a nozzle body disposed between the nozzle inlet and the nozzle outlet, the nozzle body defining a longitudinal axis and including at least two individual mixing channels in fluid communication with the nozzle inlet and with the nozzle outlet, wherein the at least two mixing channels define fluidically separate flow paths that are fluidically separate between the nozzle inlet and the nozzle outlet, at least one mixing channel of the at least two mixing channels defining a flow path having longitudinal and radial components of direction with respect to the longitudinal axis defined by the nozzle body, the nozzle inlet and the nozzle outlet being positioned at respective ends of the nozzle body.

10. The medical apparatus of claim 9, wherein each of the at least two mixing channels defines a flow path having longitudinal and radial components of direction with respect to the longitudinal axis defined by the nozzle body.

11. The medical apparatus of claim 10, wherein the nozzle body defines at least four individual mixing channels.

12. The medical apparatus of claim 9, wherein each of the at least two mixing channels defines an arcuate flow path.

13. The medical apparatus of claim 9, wherein the nozzle inlet defines an inlet chamber configured to receive the medical agent from the syringe, the inlet chamber in fluid communication with each of the at least two mixing channels.

14. The medical apparatus of claim 9, wherein the nozzle outlet defines an outlet chamber in fluid communication with the at least two individual mixing channels.

15. The medical apparatus of claim 9, wherein the nozzle inlet defines a screw thread configured to releasably couple the nozzle to the syringe.

16. The medical apparatus of claim 9, further comprising the syringe containing the medical agent, the syringe being configured to releasably couple to the mixing nozzle, wherein the medical agent comprises a liquid embolic composition including a contrast agent.

17. The medical apparatus of claim 9, further comprising a catheter coupled to the mixing nozzle.

18. The medical apparatus of claim 9, wherein the nozzle inlet includes a frangible compartment.

19. The medical apparatus of claim 18, wherein the frangible compartment includes a contrast agent.

20. The medical apparatus of claim 9, wherein the mixing nozzle further defines additional mixing channels that intersect with the at least two individual mixing channels prior to the at least two individual mixing channels reaching the nozzle outlet of the mixing nozzle.

21. The medical apparatus of claim 9, wherein an entirety of the nozzle body is between the nozzle inlet and the nozzle outlet.

22. A system comprising:
a syringe;
a liquid composition stored within the syringe; and
a mixing nozzle, the mixing nozzle including:
  a nozzle inlet configured to releasably couple to the syringe;
  a nozzle outlet; and
  a nozzle body disposed between the nozzle inlet and the nozzle outlet, the nozzle body defining at least two individual mixing channels in fluidic communication with the nozzle inlet and with the nozzle outlet, wherein the at least two mixing channels define fluidically separate flow paths that are fluidically separate between the nozzle inlet and the nozzle outlet, the nozzle inlet and the nozzle outlet being positioned at respective ends of the nozzle body.

23. The system of claim 22, wherein each of the at least two mixing channels defines a flow path having longitudinal and radial components of direction with respect to a longitudinal axis defined by the nozzle body.

24. The system of claim 22, wherein each of the at least two mixing channels defines an arcuate flow path.

25. The system of claim 24, wherein each arcuate flow path is dimensioned to diverge outwardly relative to a longitudinal axis of the nozzle body from the nozzle inlet toward a median transverse axis bisecting the nozzle body, and is dimensioned to converge inwardly from the median transverse axis toward the nozzle outlet.

26. The system of claim 22, wherein the nozzle outlet defines an outlet chamber in fluid communication with the at least two individual mixing channels whereby the mixing nozzle is configured to deliver the liquid composition from the at least two individual mixing channels to the outlet chamber for further mixing within the outlet chamber.

27. The system of claim 22, wherein the syringe comprises a plunger at least partially disposed within a fluid housing defining a housing outlet of the syringe, the plunger being configured to be advanced within the fluid housing to deliver the liquid composition through the housing outlet.

28. The system of claim 22, wherein the liquid composition includes a liquid embolic and a contrast agent.

29. The system of claim 22, wherein the mixing nozzle further defines additional mixing channels that intersect with the at least two individual mixing channels prior to the at least two individual mixing channels reaching the nozzle outlet of the mixing nozzle.

30. The system of claim 22, wherein an entirety of the nozzle body is between the nozzle inlet and the nozzle outlet.

* * * * *